United States Patent [19]

Drechsler et al.

[11] Patent Number: 6,074,654
[45] Date of Patent: Jun. 13, 2000

[54] TRANSFER RESISTANT COSMETIC COMPOSITIONS

[75] Inventors: Lee Ellen Drechsler, Cincinnati, Ohio; Thomas Elliot Rabe, Baltimore, Md.; Edward Dewey Smith, III, Mason, Ohio

[73] Assignee: The Procter & Gamble Company, Cincinnati, Ohio

[21] Appl. No.: 09/277,485

[22] Filed: Mar. 26, 1999

Related U.S. Application Data

[63] Continuation of application No. 08/732,948, Oct. 17, 1996.
[60] Provisional application No. 60/006,273, Nov. 7, 1995, provisional application No. 60/008,552, Dec. 13, 1995, and provisional application No. 60/008,553, Dec. 13, 1995.

[51] Int. Cl.$^7$ .............................. A61K 6/00; A61K 7/00; A61K 7/025
[52] U.S. Cl. .............................................. 424/401; 424/64
[58] Field of Search ........................... 424/63, 64, 78.03, 424/401

[56] References Cited

U.S. PATENT DOCUMENTS

| | | | |
|---|---|---|---|
| 2,678,878 | 2/1951 | Kauppi | 117/135.5 |
| 2,681,878 | 9/1951 | Kauppi | 167/22 |
| 3,600,186 | 8/1971 | Mattson et al. | 99/1 |
| 3,642,635 | 2/1972 | MacLeod | 252/59 |
| 3,836,647 | 9/1974 | Lange | 424/184 |
| 3,857,805 | 12/1974 | Prickril | 260/28.5 B |
| 4,005,195 | 1/1977 | Jandacek et al. | 424/180 |
| 4,005,196 | 1/1977 | Jandacek et al. | 424/180 |
| 4,725,658 | 2/1988 | Thayer et al. | 528/15 |
| 4,946,302 | 8/1990 | Uchida | 401/288 |
| 5,015,469 | 5/1991 | Yoneyama et al. | 424/59 |
| 5,051,489 | 9/1991 | O'Lenick, Jr. | 528/26 |
| 5,160,738 | 11/1992 | Macaulay et al. | 424/401 |
| 5,219,560 | 6/1993 | Suzuki et al. | 424/63 |
| 5,302,380 | 4/1994 | Castrogiovanni et al. | 424/63 |
| 5,330,747 | 7/1994 | Krzysik | 424/63 |
| 5,334,372 | 8/1994 | Kawamata et al. | 424/78.03 |
| 5,417,967 | 5/1995 | Kawamata et al. | 424/78.03 |
| 5,478,552 | 12/1995 | Hasegawa | 424/63 |
| 5,496,544 | 3/1996 | Mellul et al. | 424/78.03 |
| 5,505,937 | 4/1996 | Krzysik | 424/59 |
| 5,589,165 | 12/1996 | Yoshida et al. | 424/78.03 |
| 5,800,816 | 9/1998 | Brieva et al. | 424/63 |

FOREIGN PATENT DOCUMENTS

| | | | |
|---|---|---|---|
| 0381376A2 | 8/1990 | European Pat. Off. | A61K 7/40 |
| 0381376A3 | 8/1990 | European Pat. Off. | A61K 7/40 |
| 0515195A1 | 11/1992 | European Pat. Off. | C08L 83/06 |
| 0590192A1 | 4/1994 | European Pat. Off. | A61K 7/06 |
| 0602905A2 | 6/1994 | European Pat. Off. | A61K 7/027 |
| 0602905A3 | 6/1994 | European Pat. Off. | A61K 7/02 |
| 0610026A1 | 8/1994 | European Pat. Off. | A61K 7/032 |
| 0709083A2 | 5/1996 | European Pat. Off. | A61K 7/48 |
| 0748622A1 | 12/1996 | European Pat. Off. | A61K 7/025 |
| 2 707485 | 1/1995 | France | A61K 7/021 |
| 1913569 | 10/1969 | Germany . | |
| 38 37 473A1 | 5/1990 | Germany | A61K 7/02 |
| 61-065809 | 4/1986 | Japan | A61K 7/00 |
| 61-158913 | 7/1986 | Japan | A61K 7/02 |
| 4-045155 | 2/1992 | Japan | C08L 83/04 |
| 5-221829 | 8/1993 | Japan | A61K 7/025 |
| 6-072085 | 9/1994 | Japan | A61K 7/00 |
| 8-092034 | 4/1996 | Japan | A61K 7/02 |
| 8-092036 | 4/1996 | Japan | A61K 7/025 |
| 61-18708 | 1/1998 | Japan | A61K 7/02 |
| 2198037A | 6/1988 | United Kingdom | A46B 11/02 |
| 2 197783B | 5/1990 | United Kingdom | A46B 11/02 |
| 2211081B | 7/1991 | United Kingdom | A46B 11/02 |
| WO 93/17660 | 9/1993 | WIPO | A61K 7/48 |
| WO 96/19185 | 6/1996 | WIPO | A61K 7/02 |
| WO 97/01321 | 1/1997 | WIPO | A61K 7/021 |

OTHER PUBLICATIONS

Abstract: J5 5028–906, published Aug. 18, 1978; Derwent Publications Ltd.
Abstract: J6 2298–512A, published Jun. 19, 1986; Derwent Publications Ltd.
Abstract: JP 6107518A, Apr. 19, 1994.
Mark, J. E., Physical Properties of Polymers Handbook, AIP Press, Amer. Inst. of Physics, Chap. 16, pp. 227–239.
Vaughan, C. D., "Solubility Effects in Product, Package, Penetration and Preservation", *Cosmetics & Toiletries*, vol. 103, pp. 47–69, 1988.
General Electric, GE Silicones, Patent Technology, 7 pp.
General Electric, GE Silicones, Preliminary Data Sheet, 4 pp.

*Primary Examiner*—Thurman K. Page
*Assistant Examiner*—S. Howard
*Attorney, Agent, or Firm*—George W. Allen; Fumiko Tsuneki; John M. Howell

[57] ABSTRACT

The present invention is for cosmetic compositions applied to the lips providing significant benefits to the user. These composition comprise the combination of organosiloxane resins and fluid diorganosiloxane resins with a volatile carrier.

23 Claims, 4 Drawing Sheets

TRANSFER RESISTANT COSMETIC COMPOSITIONS

CROSS REFERENCE

This application is a continuation of Ser. No. 08/732,948, filed Oct. 17, 1996.

This application claims priority under Title 35, United States Code 119(e) from Provisional application Ser. No. 60/006,273, filed Nov. 7, 1995 and Provisional application Ser. No. 60/008,553, filed Dec. 13, 1995 and Provisional application Ser. No. 60/008,552, filed Dec. 13, 1995.

TECHNICAL FIELD

The invention is for cosmetic composition applied to the lips comprising an organosiloxane resin, a fluid diorganopolysiloxane polymer, and a volatile carrier. The composition is applied to the lips with an appropriate applicator wherein the carrier volatilizes leaving a thin, but, durable film resistant to transfer upon contact with objects such as clothing, table wear and foods, especially oily or greasy foods.

BACKGROUND ART

Cosmetic compositions applied to the lips providing transfer resistance are currently in great demand. For example, U.S. Pat. No. 5,330,747, Krzysik, issued Jul. 19, 1994, assigned to Dow Corning, discloses cosmetic compositions utilizing pressure sensitive adhesives to provide better adherence to the skin. The pressure sensitive adhesives disclosed therein comprise trimethylsilyl-endblocked benzene soluble resinous copolymers, a silanol-endblocked polydiorganosiloxane fluid and a phenyl-containing polyorganosiloxane fluid having a viscosity from 5 to 60,000 centipoises at 25° C. having 1 to 100 phenyl groups per 100 siloxane units at a level from about 0.5 to 20 parts by weight of the total weight of the resin.

Japanese Patent Application 61-161211, published Jul. 18, 1986, assigned to Shiseido, discloses cosmetic compositions having improved resistance to sweat and oil comprising 1–70% Organosiloxane resin, 10–98% volatile silicone oil, and 0.5–55% powder. The resin comprises a combination of M, D, T and Q siloxane monomers to satisfy the mean equation $RnSiO_{(4-n)/2}$ wherein R is a $C_1$ to $C_6$ or phenyl group, n equals 1 to 1.8 MQ resins having a ratio of M to Q from 0.5:1 and a molecular weight of approximately 5000 are disclosed therein.

Japanese Patent Application 61-158913, published Jul. 18, 1986, assigned to Shiseido, discloses cosmetic compositions such as those disclosed immediately above except the volatile oil is a hydrocarbon oil. This application additionally discloses in Example 2 a liquid-form lip compositions containing 40% of the MQ resin disclosed above, 20% volatile hydrocarbon oil, 20% powder, 10% glyceryl tri-isostearate and 10% red dye. This composition is reported to be non-transferable to objects such as drinking glasses.

Japanese Patent 61-18708, published Jan. 27, 1986, assigned to Pola Cosmetics, discloses 3 -dimensionally structured cosmetic compositions, preferably a mascara, comprising silicone resins and polydimethylsiloxane for improved water and oil resistance as well at stability over time. Pola asserts that this 3-dimensional structure helps to physically support ingredients such as pigments which often precipitate out without using a gelling agent. The examples contained therein disclose resins which are the combination of various organic dichlorosilane and organic trichlorosilane or "D" and "T" functional groups in ratios from 1:5 to about 5:1 wherein the total resin cross-linking is from 10% to 90%. The polydimethylsiloxane has a viscosity of not less than 1,000,000 cSt. Volatile silicone can additionally be added to the compositions disclosed therein. Lipsticks, particularly liquid-form lipsticks are not disclosed.

EP Application 0 709083 A2, Hernando et al., discloses cosmetic compositions comprising trimethylated silica, volatile solvents, non-volatile oil and a cosmetically acceptable carrier. These compositions are reported to be long lasting due to increased adherence to the skin that is not disturbed from blotting of pirspiration from the skin.

U.S. Pat. No. 5,505,937, Castrogiovanni et al., discloses cosmetic compositions comprising volatile solvents, silicone resins, wax, powder and oil. Said compositions are reported as transfer resistant as demonstrated by the use of a "Kiss Test" as disclosed at column 6, line 64.

SUMMARY OF THE INVENTION

The cosmetic compositions of the present invention are for application to the lips. Such compositions provide a durable film upon the lips that resists degradation over time. Cosmetic compositions of the present invention for application to the lips comprise:

(A) a mixture of:
 (1) a organosiloxane resin; and
 (2) a fluid diorganopolysiloxane polymer;
 wherein the ratio of (1) to (2) is from about 1:1 to about 20:1 when (2) has a viscosity from about 1,000 to about 200,000 cSt at 25° C., and the ratio of (1) to (2) is from about 1:9 to about 20:1 when (2) has a viscosity greater than 200,000 cSt at 25° C.; and (B) a volatile carrier.

BACKGROUND OF THE INVENTION

As mentioned above the unique characteristics of the present invention is due to the specific combination of the components of the present invention. These components include organosiloxane resins and fluid diorganopolysiloxane polymers and a volatile carrier.

In additional to their compositional structure, compositions of the present invention are differentiated from the art in terms of their physical characteristics of the film that is formed once the composition is applied. In vitro tests have been developed to clearly demonstrate the distinctiveness of the present invention in terms of the physical characteristics of the films formed from such compositions.

Films formed from cosmetic compositions exhibit a degree of transfer resistance directly proportional to the hardness and solvent-resistance of the film. This hardness can be expressed as a function of the dry blot and rub test. The solvent-resistance, or resistance to being solvated by fluids, can be expressed as a function of an oil blot and rub test, both tests described below. The optimum test conditions to reliably correlate these tests to the physical characteristics of the composition requires that the film be dry. But dry it is meant that at least 90% of the volatile carrier of the claimed cosmetic composition has evaporated.

Dry Blot and Rub Test Method

This test predicts the ability of a cosmetic film to resist color transfer to objects contacting the skin. Such objects include clothing, hankerchiefs or tissues, napkins and implements such as cups, glasses and table wear.

Equipment (1) Datacolor Spectraflash 500 spectral analyzer with 30 mm sampler port and software to calculate % reflectance over a wavelength range of 400 nm to 700 nm;

(2) 2×3 inch glass slide;

(3) Collagen sausage casing such as Nippi Casing F Grade;

(4) Constant humidity chamber adjusted to 95% relative humidity;

(5) Utility Knife;

(6) Ruler;

(7) Single-sided adhesive tape;

(8) Double-sided adhesive tape;

(9) 25 micron thickness slot draw-down bar;

(10) White Styrofoam dinner plate such as Amoco Selectables™ Plastic DL® Tableware;

(11) 1.5 inch diameter circular metal punch; and

Figure 1:
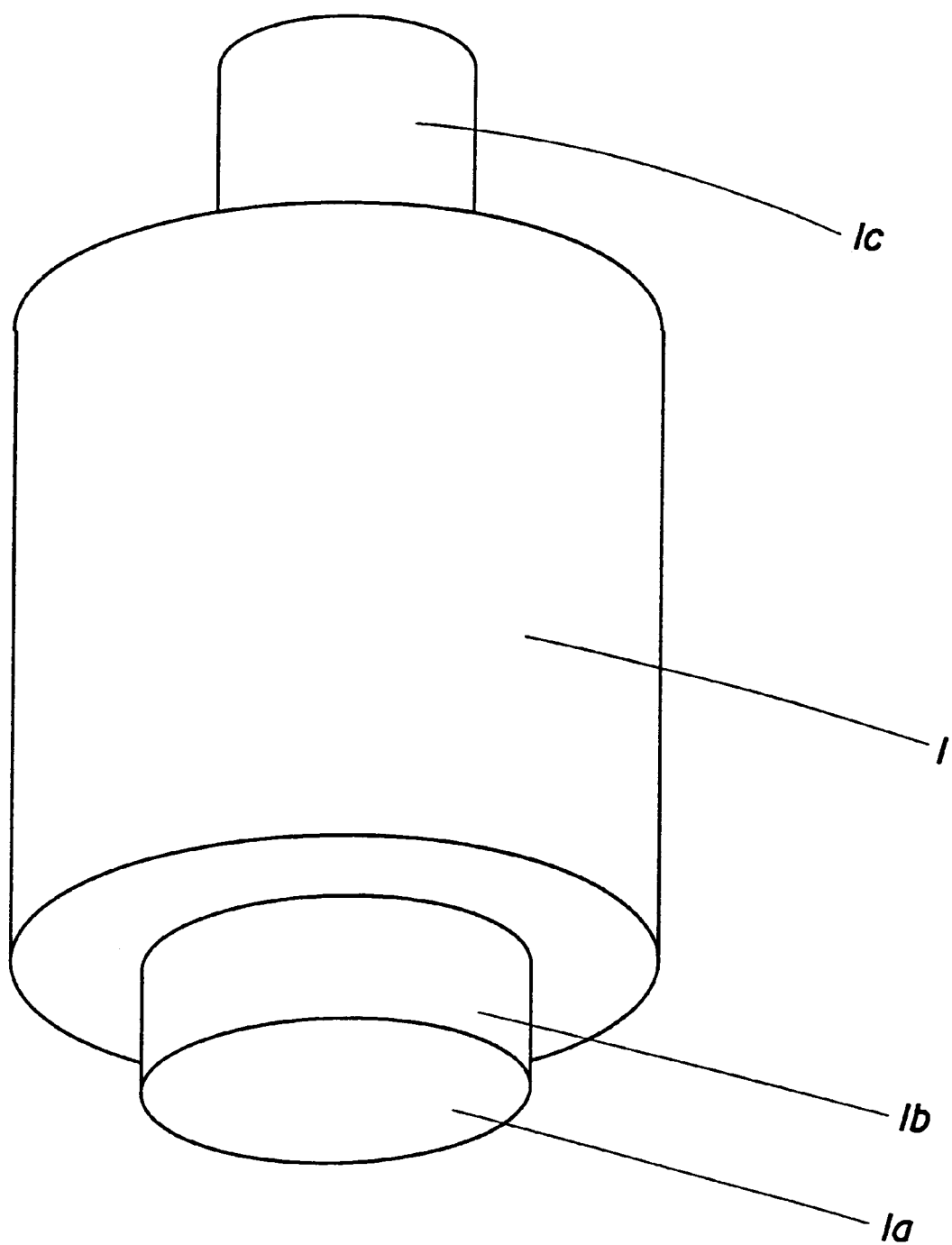
FIG. 1 is a planar view of the apparatus or weight disclosed in the test method section below to conduct the dry and oil blot/rub tests on the claimed compositions.

(12) 2 kilogram weight with attached aluminum disk illustrated in FIG. 1.

Procedure (1) Prepare a 3×4 inch sheet of collagen sausage casing by hydrating it in a 90% relative humidity chamber for at least two hours.

(2) Remove the collegen sheet to ambient conditions and immediately wrap tightly around the entire 2×3 inch slide. Attache the collage sheet to the bottom of the slide using adhesive tape. The top collagen surface should be flat and free of wrinkles.

(3) Allow the collagen-wrapped slide to equilibrate at ambient conditions for 24 hours.

(4) Cut a 2×3 inch rectangle from a white Styrofoam dinner plate using a ruler and a utility knife.

(5) Draw down thin, uniform films of cosmetic on the collagen and white Styrofoam surfaces. The film areas on each should be about 2×2 inches.

(6) Allow the cosmetic samples on both the collagen and Styrofoam surfaces to sit at ambient conditions for 24 hours.

(7) Cut two disks from a clean, white Styrofoam dinner plate using a 1.5 inch diameter circular punch. The surface and edges of each disk should be smooth and even.

(8) Set one disk aside for use as described in step 13.

(9) Firmly attach with double-sided adhesive disk (1a) from step (7) to bottom surface (1b) of the 2 kg weight (1) of FIG. 1.

(10) Set the weight on top of cosmetic sample applied to the collagen surface from step 6 above so that disk (1a) is in contact with the film. It is important to position the weight gently so that excess force beyond 2 kg is not applied.

(11) Grasping the top (1c) of the 2 kg weight (1) of FIG. 1, carefully rotate the disk through 360° while maintaining the 2 kg force on the film. Do not lift or press the weight into the film during the rotating motion to the weight. The entire 360° rotation should be completed within a time interval between 3 and 5 seconds.

(12) Lift the weight straight up off the film surface. Carefully remove the disk (1a) of FIG. 2 from the weight (1) avoiding damage to the disk.

(13) Measure the percent reflectance of the drawn-down cosmetic film on Styrofoam substrate from step 6 (herein referred to as A), the clean white Styrofoam disk from step 8 (herein referred to as B), and the blot/rub tested Styrofoam disk from steps 9–12 (herein referred to as C) over a wavelength range of 400 nm to 700 nm using a Datacolor spectral analyzer with a 30 mm sample port, with lighting conditions of D65/10 deg.

(14) Choose the wavelength of minimum reflectance for the dry blot/rub tested disk.

(15) At this wavelength, calculate the normalized percent reflectance value of the dry blot/rub tested disk using the following equation:

$$\text{Normalized Percent Reflectance } (NPR_{dry}) = 1 - [(C-B) \div (A-B)] \times 100$$

A high normalized percent reflectance value corresponds to very little color transfer during dry blotting and rubbing insults. Steps (1) through (15) are repeated three times for each cosmetic formula specimens per cosmetic formula tested by each method respectively. The average of the three $NPR_{dry}$ values is determined; herein referred to as Average Normalized Percent Reflectance; hereinafter referred to as $ANPR_{dry}$. Compositions of the present invention have an $ANPR_{dry}$ of about 50% and greater, preferably about 65% and greater, most preferably about 75% and greater.

Oil Blot and Rub Test Method

This test predicts the ability of a cosmetic film to resist color transfer to oil fingers or objects such as oily foods.

Equipment (1) Datacolor Spectraflash 500 spectral analyzer with 30 mm sample port and software to calculate % reflectance over a wavelength range of 400 nm to 700 nm;

(2) 2×3 inch glass slide;

(3) Collagen sausage casing such as Nippi Casing F Grade;

(4) Constant humidity chamber adjusted to 95% relative humidity;

(5) Utility Knife;

(6) Ruler;

(7) Single-sided adhesive tape;

(8) Double-sided adhesive tape;

(9) 25 micron thickness slot draw-down bar;

(10) White Styrofoam dinner plate such as Amoco Selectables™ Plastic DL® Tableware;

(11) 1.5 inch diameter circular metal punch; and

(12) 2 kilogram weight with attached aluminum disk illustrated in FIG. 1

(13) Olive oil

(14) Brush-tip cosmetic applicator

(15) Lint-Free Wiper, such as Kimwipes® EX-L

Procedure (1) Prepare a 3×4 inch sheet of collagen sausage casing by hydrating it in a 90% relative humidity chamber for at least two hours.

(2) Remove the collegen sheet to ambient conditions and immediately wrap tightly around the entire 2×3 inch slide. Attach the collagen sheet to the bottom of the slide using adhesive tape. The top collagen surface should be flat and free of wrinkles.

(3) Allow the collagen-wrapped slide to equilibrate at ambient conditions for 24 hours.

(4) Cut a 2×3 inch rectangle from a white Styrofoam dinner plate using a ruler and a utility knife.

(5) Draw down thin, uniform films of cosmetic on the collagen and white Styrofoam surfaces. The film areas on each should be about 2×2 inches.

(6) Allow the cosmetic samples on both the collagen and Styrofoam surfaces to sit at ambient conditions for 24 hours.

(7) Using a pipet, drop 0.1 grams of olive oil onto the dried film. This weight should correspond to approximately three drops of oil.

(8) Distribute the oil evenly over the film surface with a cosmetic brush applicator, brushing lightly.

(9) Allow the oil to remain on the film undisturbed for 30 minutes.

(10) Using a lint-free wiper, carefully blot excess oil from the film surface. Apply as little pressure as possible during this step.

(11) Cut two disks from a clean, white Styrofoam dinner plate using a 1.5 inch diameter circular punch. The surface and edges of each disk should be smooth and even.

(12) Set one disk aside for use as described in step 13.

(13) Firmly attach with double-sided adhesive tape disk (1a) from step (7) to bottom surface (1b) of the 2 kg weight (1) of FIG. 1.

(14) Set the weight on top of cosmetic sample applied to the collagen surface from step 6 above so that disk (1a) is in contact with the film. It is important to position the weight gently so that excess force beyond 2 kg is not applied.

(15) Grasping the top (1c) of the 2 kg weight (1) of FIG, 1, carefully rotate the disk through 360° while maintaining the 2 kg force on the film. Do not lift or press the weight into the film during the rotating motion to the weight. The entire 360° rotation should be completed within a time interval between 3 and 5 seconds.

(16) Lift the weight straight up off the film surface. Carefully remove the disk (1a) of FIG. 1 from the weight (1) avoiding damage to the disk.

(17) Measure the percent reflectance of the drawn-down cosmetic film on Styrofoam substrate from step 6 (herein referred to as A), the clean white Styrofoam disk from step 8 (herein referred to as B), and the blot/rub tested Styrofoam disk from steps 9–12 (herein referred to as C) over a wavelength range of 400 nm to 700 nm using a Datacolor spectral analyzer with a 30 mm sample port, with lighting conditions of D65/10 deg.

(18) Choose the wavelength of minimum reflectance for the oil blot/rub tested disk.

(19) At this wavelength, calculate the normalized percent reflectance value of the oil blot/rub tested disk using the following equation:

$$\text{Normalized Percent Reflectance (NPR}_{oil}) = 1 - [(C-B) \div (A-B)] \times 100$$

A high normalized percent reflectance value corresponds to very little color transfer during oil blotting and rubbing insults. Steps (1) through (15) are repeated three times for each cosmetic formula specimens per cosmetic formula tested by each method respectively. The average of the three $NPR_{oil}$ values is determined; herein referred to as Average Normalized Percent Reflectance; hereinafter referred to as $ANPR_{oil}$. Compositions of the present invention have an $ANPR_{oil}$ of about 50% and greater, preferably about 65% and greater, most preferably about 75% and greater.

In addition to the embodiment of the invention disclosed above, a second embodiment of the present invention demonstrates flexibility as well as hardness of the film. While hardness is critical to transfer resistance as discussed above, flexibility or the ability of the film to stretch and move with the lips is critical towards providing improved long wear benefits of the composition.

As above, a test has been developed to characterize the flexibility the film formed from the compositions of the present invention. As previously mentioned, the optimum test conditions to reliably correlate this test to the physical characteristics of the composition requires that the film be dry. By dry it is meant that at least 90% of the volatile carrier of the claimed cosmetic composition has evaporated. This test of the film formed from the composition of the present invention is as follows:

Flexibility Test Method

Flexibility is measured by the latex stretch test. This test predicts the ability of the color film to resist flaking or peeling types of failure after application by movement of the skin during normal activities. The latex stretch test method is as follows:

Equipment (1) Ansell Edmont Industrial technicians unlined gloves (12" length, 17 mil) USDA Accepted #390, Size 9;

(2) A disposable lip brush such as those available from La Femme Cosmetics, Inc. of L.A.

Figure 2:
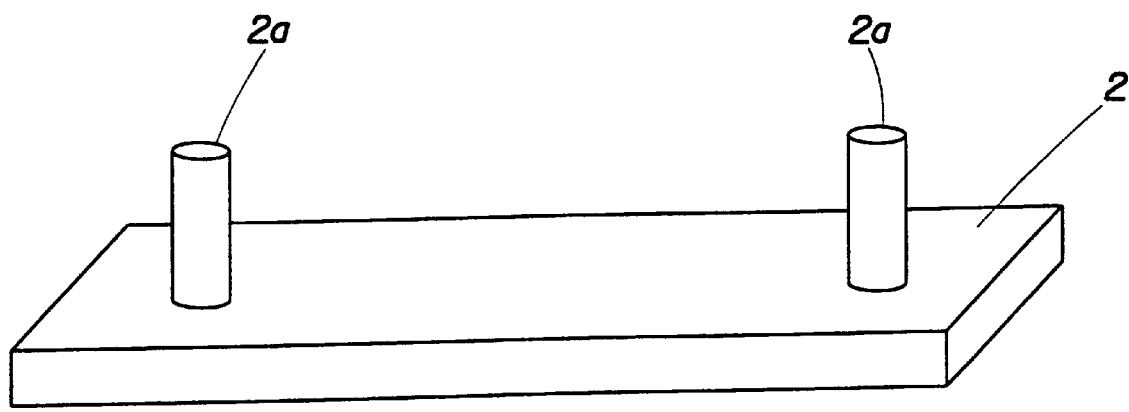
FIG. 2 is a planar view of the apparatus disclosed in the test method section below for conducting the film flexibility test on the claimed compositions.
Figure 3:
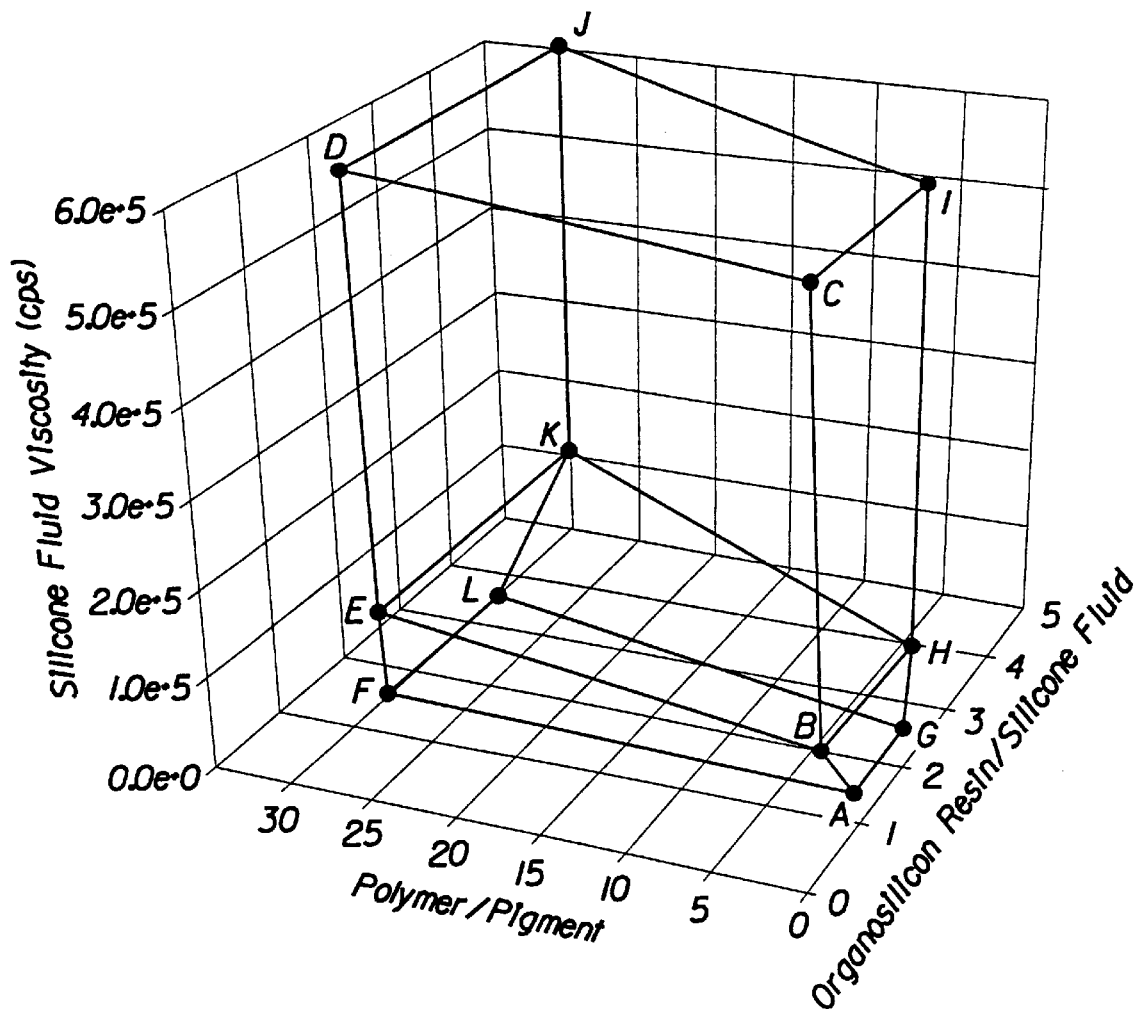
FIG. 3 is a three dimensional graphical representation of the formulation space in terms of the components that define the present invention.
Figure 4:
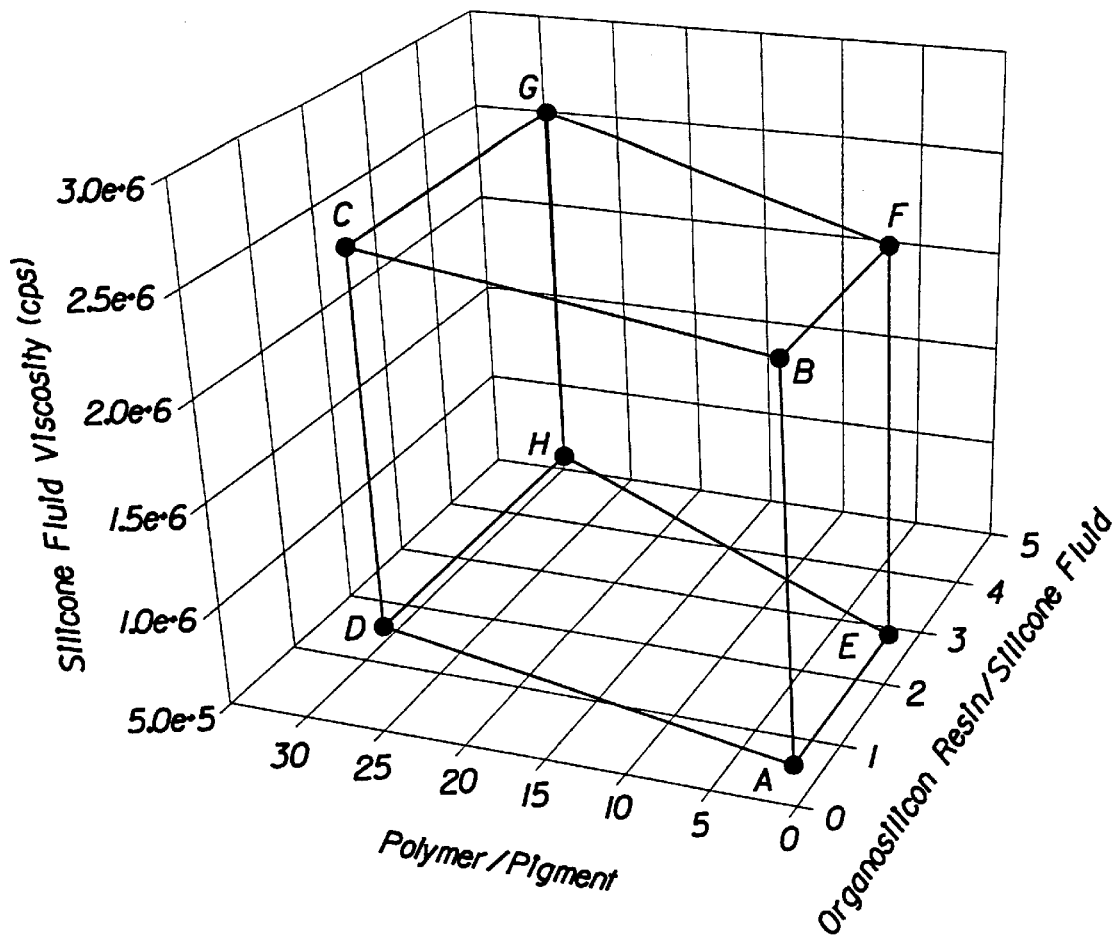
FIG. 4 is a three dimensional graphical representation of the formulation space in terms of the components that define the present invention.

(3) Analytical balance (4 decimal places);

(4) Ruler; and (5) An apparatus as illustrated in FIG. 2. Said apparatus can be constructed from Lucite sheet and rod stock wherein posts 2a are approximately 6 inches apart.

Procedure (1) Cut a 1 inch wide band from the the wrist area of the glove, avoiding the ribbing and thumb.

(2) Mark off a 1×1 inch block in the center of the band, avoiding the embossed number.

(3) Weigh and record the weight of the latex band; hereinafter referred to as A.

(4) Determine the initial weight of the cosmetic to be applied to the band in order to produce a dried film weighing 20 mg. This is determined by dividing 20 mg by the weight percent of non-volatile material present in the cosmetic. For example, 50 mg of a cosmetic with 40% non-volatile content must be applied to the band in order to yield a 20 mg dried film.

(5) Using a disposable lip brush, evenly apply the amount of cosmetic determined in step (4) over the 1×1 inch area of the band as marked in step (2).

(6) Immediately weigh and record the combined weight of the latex band and applied cosmetic. The wet film weight is calculated by subtracting A from the combined weight of the latex band and applied cosmetic.

(7) Allow the sample on the latex band from step (6) to sit at ambient room conditions for 24 hours.

(8) Weigh and record the combined weight of the latex band A and the applied cosmetic film; hereinafter referred to as B. Subtract A from B to determine the dried film weight C. This weight should be 20±2 mg.

(9) Stretch the band just enough to slip over the posts (2a) of apparatus (1) of FIG. 2. Gently manipulate the latex band on the posts so that the stretched film length is 1.75 inches.

(10) Upon observing loosened film pieces on the latex band, remove the film pieces from the latex band by vigorously wiping a disposable lip brush across the surface of the film.

(11) Carefully remove the latex band from the posts (2a) allowing it to returns to its approximate original shape.

(12) Record the weight of the latex band (with the remaining cosmetic); herein referred to as D.

(13) Calculate the percent weight loss of the cosmetic film using the following equation:

Percent Weight Loss (PWL)=[$(D-A)$÷$(B-A)$]×100

Steps (1) through (13) are repeated three times for each cosmetic formula tested. The average of the three PWL values is determined; herein referred to as Average Percent Weight Loss; or APWL. Low APWL values corresponds to flexible films having desirable adhesive and cohesive balance of the film. The APWL for compositions of the present invention is 30% and less, preferably about 15% and less, most preferably about 10%.

The second embodiment of the present invention that meets both the flexibility test and oil blot/rub tests comprises:

a. an organosiloxane resin;
b. a fluid diorganopolysiloxane polymer;
c. a pigment; and
d. a volatile carrier capable of solubilizing said organosiloxane resins;

wherein the fluid diorganopolysiloxane polymer has a viscosity greater than 1,000 cSt at 25° C., the ratio of the combination of organosiloxane resin and fluid diorganopolysiloxane polymer to pigment is from about 1:1 to about 30:1 and the ratio of organosiloxane resin to fluid diorganopolysiloxane polymer is from about 1:10 to about 3.5:1. Preferably the fluid diorganopolysiloxane polymer has a viscosity greater than 600,000 cSt at 25° C., most preferably greater than 1,000,000 cSt.

Organosiloxane Resins

The organosiloxane resins used in the present invention comprise combinations of $R_3SiO_{1/2}$ "M" units, $R_2SiO$ "D" units, $RSiO_{3/2}$ "T" units, $SiO_2$ "Q" units in ratios to each other that satisfy the relationship $R_nSiO_{(4-n)/2}$ where n is a value between 1.0 and 1.50 and R is a methyl group. Note that a small amount, up to 5%, of silanol or alkoxy functionality may also be present in the resin structure as a result of processing. The organosiloxane resins must be solid at about 25° C. and has a molecular weight range from about 1,000 to about 10,000 grams/mole. The resin is soluble in organic solvents such as toluene, xylene, isoparaffins, and cyclosiloxanes or the volatile carrier, indicating that the resin is not sufficiently crosslinked such that the resin is insoluble in the volatile carrier. Particularly preferred are resins comprising repeating monofunctional or $R_3SiO_{1/2}$ "M" units and the quadrafunctional or $SiO_2$ "Q" units, otherwise known as "MQ" resins as disclosed in U.S. Pat. No. 5,330,747, Krzysik; issued Jul. 19, 1994, incorporated herein by reference. In the present invention the ratio of the "M" to "Q" functional units is preferably about 0.7 and the value of n is 1.2. Organosiloxane resins such as these are commercially available such as Wacker 803 and 804 available from Wacker Silicones Corporation of Adrian Mich., and G. E. 1170-002 from the General Electric Company.

The siloxane resins are used in the present invention at levels from about 10% to about 95%, preferably from about 55% to about 80% and most preferably from about 60% to about 70% of the total amount of Organosiloxane resin and fluid diorganopolysiloxane polymers.

Fluid Diorganopolysiloxane Polymers

The present invention employs a fluid diorganopolysiloxane polymers to be combined with the organosiloxane resins disclosed above. Said fluid diorganopolysiloxane polymers useful in the present invention span a large range of viscosities; from about 1,000 to about 10,000,000 centistokes (cSt) at 25° C.

The fluid diorganopolysiloxane polymers of the present invention comprise repeating units, wherein said units correspond to the formula ($R_2SiO$), where R is a monovalent hydrocarbon radical containing from 1 to 6 carbon atoms, preferably selected from the group consisting of methyl, ethyl, propyl, isopropyl, butyl, isobutyl, t-butyl, amyl, hexyl, vinyl, allyl, cyclohexyl, phenyl, fluoroalkyl and mixtures thereof. The diorganopolysiloxane fluids employed in the present invention may contain one or more of these hydrocarbon radicals as substituents on the siloxane polymer backbone. The diorganopolysiloxane fluids may be terminated by triorganosilyl groups of the formula ($R'_3Si$) where R' is a radical selected from the group consisting of monovalent hydrocarbons containing from 1–6 carbon atoms, hydroxyl groups, alkoxyl groups and mixtures thereof. When a diorganopolysiloxane polymer fluid is present, it is essential that it be compatible in solution with the organosiloxane resin material and the volatile carrier. The term "compatible" refers to the formation of a single phase solution when the diorganopolysiloxane fluid, organosiloxane resin and volatile carrier are mixed together in ratios required for a specific formulation. A particularly preferred fluid diorganosiloxane polymer is poly(dimethylsiloxane), herein referred to as PDMS.

Volatile Carriers

In the present invention, the combination of the organosiloxane resin and fluid diorganosiloxane polymer above must be easily transferred to the lip surface using a package/applicator. To achieve delivery, it is necessary that this combination above be incorporated into a carrier, specifically a volatile carrier which quickly volatilizes from the surface of the lips leaving the above-discussed thin-durable film. The volatile carrier must solubilize the organosiloxane resin and the fluid diorganosiloxane polymer.

The volatile carrier comprises from about 10% to about 90%, preferably from about 15% to about 80%, and most preferably from about 20% to about 70% of the composition. The volatile carrier of the present invention are selected from the group consisting of volatile hydrocarbons, volatile silicones and mixtures thereof.

Hydrocarbon oils useful in the present invention include those having boiling points in the range of 60–260° C., more preferably hydrocarbon oils having from about $C_8$ to about $C_{20}$ chain lengths, most preferably $C_8$ to $C_{20}$ isoparaffins. Of these isoparriffins most preferred are selected from the group consisting of isododecane, isohexadecane, isoeocosane, 2,2,4-trimethylpentane, 2,3-dimethylhexane and mixtures thereof. Most preferred is isododecane, available as for example Permethyl 99A from Permethyl Corporation corresponding to the formula:

Preferred volatile silicone fluids include cyclomethicones having 3, 4 and 5 membered ring structures corresponding to the formula:

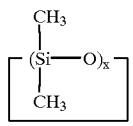

where X is from about 3 to about 6. Said volatile silicones include 244 Fluid, 344 Fluid and 245 Fluid, and 345 Fluid all from Dow Corning Corporation.

Pigments

Pigments suitable for use herein are all inorganic and organic colors/pigments suitable for use in lip composition compositions. These are usually aluminum, barium or calcium salts or lakes. Lakes are either a pigment that is extended or reduced with a solid diluent or an organic pigment that is prepared by the precipitation of a water-soluble dye on an adsorptive surface, which usually is aluminum hydrate. A lake also forms from precipitation of an insoluble salt from an acid or basic dye. Calcium and barium lakes are also used herein.

Preferred lakes of the present invention are Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

Other colors and pigments can also be included in the lip compositions, such as pearls, titanium oxides, Red 6, Red 21, Blue 1, Orange 5, and Green 5 dyes, chalk, talc, iron oxides and titanated micas.

Compositions of the present invention contain a sufficient pigments to provide the look sought by the user. The pigments are used herein at levels relative to the level of the fluid diorganopolysiloxane polymer disclosed above. This level is expressed as a ratio of the combination of fluid diorganopolysiloxane polymer and organosiloxane resin to pigment. In the present invention this ratio is from about 1:1 to about 30:1, preferably from about 1.5:1 to about 15:1, and most preferably from about 2:1 to about 10:1.

There are a number of other ingredients approved for use in the cosmetic art that may be used in copmositions of the present invention. Such ingredients are those approved for use in cosmetics and can be found listed in reference books such as the CTFA Cosmetic Ingredient Handbook, Second Edition, The Cosmetic, Toiletries, and Fragrance Association, Inc. 1988, 1992. Said materials may be used provided their inclusion does not significantly disrupt the composition once it has been applied to the skin wherein a film has been formed. Said ingredients include waxes, fragrances, flavor oils, skin care ingredients such as sunscreen, emulsifiers and the like. Hypoallergenic compositions can be made into the present invention where said compositions do not contain fragrances, flavor oils, lanolin, sunscreens, particularly PABA, or other sensitizers and irritants.

Waxes may be used in the present invention provided they are used at levels which does not interfere with film formation process. Generally waxes are not used in the present invention higher than about 2% of the composition.

Waxes are defined as lower-melting organic mixtures or compounds of high molecular weight, solid at room temperature and generally similar in composition to fats and oils except that they contain no glycerides. Some are hydrocarbons, others are esters of fatty acids and alcohols. Waxes useful in the present invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof.

The specific waxes useful in the present invention are selected from the group consisting of synthetic waxes, ozokerite, jojoba esters, "Unilins", available from Petrolite Corporation, "Ganex" alkylated polyvinylpyrrolidines available from the ISP Company, fatty alcohols from C22 to C50 and mixtures thereof. Synthetic waxes include those disclosed in Warth, *Chemistry and Technology of Waxes,* Part 2, 1956, Reinhold Publishing; herein incorporated by reference. The waxes most useful herein are selected from the $C_8$ to $C_{50}$ hydrocarbon waxes. Such waxes include long chained polymers of ethylene oxide combined with a dihydric alcohol, namely polyoxyethylene glycol. Such waxes include carbowax available from Carbide and Carbon Chemicals company. Other synthetic waxes include long-chained polymers of ethylene with OH or other stop length grouping at end of chain. Such waxes include the Fischer-Tropsch waxes as disclosed in the text disclosed above at pages 465–469 and include Rosswax, available from Ross company and PT-0602 available from Astor Wax Company.

Flavor oils such as peppermint oil, orange oil, citrus oil, or wintergreen oil can be used along with an alcohol or glycerine. Flavor oils are usually mixed in a solvent such as ethanol to dilute the flavor. The flavor oils useful herein can be derived from natural sources or be synthetically prepared. Generally, flavor oils are mixtures of ketones, alcohols, fatty acids, esters and terpenes. The term "flavor oil" is generally recognized in the art to be a liquid which is derived from botanical sources, i.e. leaves, bark, or skin of fruits or vegetables, and which are usually insoluble in water. The level of flavor oil used can range from 0% to about 5%, preferably from 0% to about 1% of the lip composition composition.

Emulsifiers may be used as coupling agents which have an affinity for the hydrophilic and hydrophobic phases of lip compositions of this invention. Such emulsifiers include those routinely used in cosmetics and are found in the CTFA. Once such commercially available emulsifier is Dow Corning 3225C available from Dow Corning.

Skin care active ingredients in both water soluble and water insoluble forms can be added to the lip compositions. Said ingredients may include fat soluble vitamins, sunscreens and pharmaceutically active ingredients. These skin care active ingredients include glycerine, zinc oxide; chamomile oil; ginko biloba extract; pyroglutamic acid, salts or esters; sodium hyaluronate; 2-hydroxyoctanoic acid; sulfur, salicylic acid; carboxymethyl cysteine, water, propylene glycol and mixtures thereof.

Complimentary products may be used in conjunction with the present invention to compliment the compositions and improve its aesthetic appeal to the user.

It is specifically envisioned that the complementary products used in the present invention manner wherein such a product is applied over the film formed after application of the cosmetic composition of the present invention. For example in the case of lip compositions, a complimentary product may be utilized to enhance the gloss and shine of the lips and provide a lubricious feeling. Such products, otherwise known as an "overcoat" or "topcoat" may be in a stick or liquid form and can include any that are commercially available or to be developed, provided the aggregate of the materials comprising the overcoat does not significantly disrupt the composition of the present invention. The overcoat compositions may be clear or transparent or may contain dyes and/or colorants that when viewed along with the overcoat, produce a desired color.

One such material that has been shown to be quite useful in formulating complimentary products is polyol polyesters, such as sucrose polyesters (herein referred to as SPE'S). SPE's are synthesized molecules derived from sugar and vegetable oil and have been extensively disclosed in the patent literature in context of a non-digestible oils. Such compositions are generally disclosed in U.S. Pat. Nos. 3,600,186, issued Aug. 17, 1971; 4,005,195, issued Jan. 25, 1977; 4,005,196, issued Jan. 25, 1977; all assigned to the Procter & Gamble Company and all herein incorporated by reference.

It has found that overcoat compositions having a significant level of SPE'S are incompatible with the lip composition of the present composition wherein upon their application, the cosmetic composition of the present invention is not disrupted.

Examples of complimentary products for cosmetic lip compositions of the present invention, which may be used with the lip composition of the present invention are as follows:

EXAMPLE 1

| Ingredient | Weight (%) |
| --- | --- |
| SPE Cottonate | 89.75 |
| SPE Behenate | 5.05 |
| Mica[1] | 5.05 |
| Propylparaben | 0.10 |
| Ethylene Brassylate | 0.05 |

[1]-Sericite available from U.S. Cosmetics Corporation

Combine all ingredients in a vessel and heat to 90° C. while stirring constantly with a propeller mixer. When the SPE Behenate has completely melted and the mixture is homogeneous, remove from heat and cool to room temperature. The mixture should be stirred constantly during cooling. Transfer the resulting fluid to individual packages.

EXAMPLE 2

| Ingredient | Weight (%) |
| --- | --- |
| SPE Cottonate | 88.30 |
| SPE Behenate | 4.70 |
| Mica[1] | 4.65 |
| Propylparaben | 0.15 |
| Methyparahen | 0.15 |
| Ethylene Brassylate | 0.05 |

[1]-Sericite available from U.S. Cosmetics Corporation

Combine all ingredients in a vessel and heat to 90° C. while stirring constantly with a propeller mixer. When the SPE Behenate has completely melted and the mixture is homogeneous, remove from heat and cool to room temperature. The mixture should be stirred constantly during cooling. Transfer the resulting fluid to individual packages.

EXAMPLE 3

| Ingredient | Weight (%) |
| --- | --- |
| Castor Oil | 89.75 |
| Glycerin/Diethylene Glycol/Adipate Crosspolymer[1] | 5.00 |
| Ozokerite | 5.00 |
| Propylparaben | 0.10 |
| Methyparaben | 0.10 |
| Ethylene Brassylate | 0.05 |

[1]-available as Lexorez 100 from Inolex Chemical Company.

Combine all ingredients in a vessel and heat to 90° C. while stirring constantly with a propeller mixer. When the ozokerite has completely melted and the mixture is homogeneous, remove from heat and cool to room temperature. The mixture should be stirred constantly during cooling. Transfer the resulting fluid to individual packages.

EXAMPLE 4

| Ingredient | Weight (%) |
| --- | --- |
| SPE Cottonate | 85.85 |
| SPE Behenate | 14.00 |
| Propylparaben | 0.10 |
| Ethylene Brassylate | 0.05 |

Combine all ingredients in a vessel and heat to 90° C. while stirring constantly with a propeller mixer. When the SPE Behenate has completely melted and the mixture is homogeneous, remove from heat and pour into lipstick molds. Cool to approximately −5° C. before de-molding and placing in an appropriate package.

EXAMPLE 5

| Ingredient | Weight (%) |
| --- | --- |
| Group A: | |
| SEFA Cottonate | 84.58 |
| SEFA Behenate | 14.36 |
| Ganex Wax WP-660[1] | 0.86 |
| Propylparaben | 0.10 |
| BHT | 0.05 |
| Group B: | |
| Ethylene Brassylate | 0.05 |

[1]-Ganex Wax available from ISP Technologies, Inc.

Combine Group A ingredients together and mix well with a spatula. Heat the Group A mixture until all solids melt (approx. 90° C.), stirring occasionally while heating. Add Group B ingredients and mix for 5 minutes with a propeller mixer. Do not let the temperature rise above 90° C. When the mixture of Groups A and B ingredients in homogeneous, pour the molten material into seasoned lipstick molds. Chill the filled molds at 5° C. for approximately 20 minutes. Remove the molds to ambient conditions and demold sticks. Place sticks in lipstick cases.

EXAMPLE 6

| Ingredient | Weight (%) |
|---|---|
| Group A: | |
| SEFA Cottonate | 70.67 |
| SEFA Behenate | 14.13 |
| Talc | 15.00 |
| Propylparaben | 0.10 |
| BHT | 0.05 |
| Group B: | |
| Ethylene Brassylate | 0.05 |

Combine Group A ingredients together and mix well with a spatula. Heat the Group A mixture until all solids melt (approx. 90° C.), stirring occasionally while heating. Add Group B ingredients and mix for 5 minutes with a propeller mixer. Do not let the temperature rise above 90° C. When the mixture of Groups A and B ingredients is homogeneous, pour the molten material into seasoned lipstick molds. Chill the filled molds at 5° C. for approximately 20 minutes. Remove the molds to ambient conditions and demold sticks. Place sticks in lipstick cases.

EXAMPLE 7

| Ingredient | Weight (%) |
|---|---|
| Group A: | |
| SEFA Cottonate | 83.17 |
| SEFA Behenate | 16.63 |
| Propylparaben | 0.10 |
| BHT | 0.05 |
| Group B: | |
| Ethylene Brassylate | 0.05 |

Combine Group A ingredients together and mix well with a spatula. Heat the Group A mixture until all solids melt (approx 90° C.), stirring occasionally while heating. Add Group B ingredients and mix for 5 minutes with a propeller mixer. Do not let the temperature rise above 90° C. When the mixture of Groups A and B ingredients is homogeneous, pour the molten material into seasoned lipstick molds. Chill the filled molds at 5° C. for approximately 20 minutes. Remove the molds to ambient conditions and demold sticks. Place sticks in lipstick cases.

EXAMPLE 8

| Ingredient | Weight (%) |
|---|---|
| Group A: | |
| SEFA Cottonate | 75.02 |
| SEFA Behenate | 13.58 |
| Talc | 7.50 |
| Ganex Wax WP-660[1] | 0.50 |
| Propylparaben | 0.15 |
| BHT | 0.05 |
| Group B: | |
| Glycerin | 3.00 |
| Methylparaben | 0.15 |
| Group C: | |
| Ethylene Brassylate | 0.05 |

[1]Ganex Wax available from ISP Technologies, Inc.

Combine Group A ingredients together and mix well with a spatula. Heat the Group A mixture until all solids melt (approx. 90° C.), stirring occasionally while heating. Combine Group B ingredients together and mix well with a spatula. Heat the Group B mixture to approximately 90° C. Combine Group A and group B mixtures and homogenize for 5 minutes at 5000 rpm. Add Group C ingredients and mix for 5 minutes with a propeller mixer. When the mixture is homogeneous, pour the molten material into seasoned lipstick molds. Chill the filled molds at 5° C. for approximately 20 minutes. Remove the molds to ambient conditions and demold sticks. Place sticks in lipstick cases.

EXAMPLE 9

| Ingredient | Weight (%) |
|---|---|
| Group A: | |
| SEFA Cottonate | 59.55 |
| SEFA Behenate | 12.50 |
| Talc | 7.50 |
| Propylparaben | 0.15 |
| Vitamin E Linoleate | 0.10 |
| Group B: | |
| Water | 10.00 |
| Propylene Glycol | 5.00 |
| Glycerin | 5.00 |
| Methylparaben | 0.15 |
| Group C: | |
| Ethylene Brassylate | 0.05 |

Combine Group A ingredients together and mix well with a spatula. Heat the Group A mixture until all solids melt (approx. 90° C.), stirring occasionally while heating. Combine Group B ingredients together and mix well with a spatula. Heat the Group B mixture to approximately 90° C. Combine Group A and Group B mixtures and homogenize for 2 minutes at 5000 rpm. Add Group C ingredients and mix for 5 minutes with a propeller mixer. When the mixture is homogeneous, pour the molten material into seasoned lipstick molds. Chill the filled molds at 5° C. for approximately 20 minutes. Remove the molds to ambient conditions and demold sticks. Place sticks in lipstick cases.

EXAMPLE 10

| Ingredient | Weight (%) |
|---|---|
| Group A: | |
| SEFA Cottonate | 84.01 |
| SEFA Behenate | 15.23 |
| Ganex Wax WP-660[1] | 0.54 |

| Ingredient | Weight (%) |
|---|---|
| Propylparaben | 0.11 |
| BHT | 0.05 |
| Group B: | |
| Ethylene Brassylate | 0.06 |

[1] Ganex Wax available from ISP Technologies, Inc.

Combine Group A ingredients together and mix well with a spatula. Heat the Group A mixture until all solids melt (approx 90° C.), stirring occasionally while heating. Add Group B ingredients and mix for 5 minutes with a propeller mixer. Do not let the temperature rise above 90° C. When the mixture of Groups A and B ingredients is homogeneous, pour the molten material into seasoned lipstick molds. Chill the filled molds at 5° C. for approximately 20 minutes. Remove the molds to ambient conditions and demold sticks. Place sticks in lipstick cases.

METHODS OF USING THE INVENTION

The method of the present invention is straight forward. The user applies the composition of the present invention from a suitable liquid cosmetic applicator directly onto the lips. One such applicator used for liquid products is a liquid pen package disclosed in British Patent 21198037, issued May 9, 1990, assigned to Mitsubishi Pencil Co., Ltd. of Japan. An alternative package is one where an wand is dipped into a reservoir wherein the composition on the tip of the wand is applied to the lips. Such packages are disclosed in Japanese Utility Model 64 000822 Y2, To Shiseido.

Another cosmetic dispenser that is useful for the present invention is a unidirectional twist-up dispensing device with incremental dosing as disclosed in co-pending patent application entitled "Simplified Unidirectional Twist-Up Dispensing Device With Incremental Dosing", Richard L. Horstman et al., filed Oct. 25, 1996 to Procter and Gamble. Such a twist-up dispensing device can include a hollow housing defining a chamber having an open dispensing end and a piston located within the chamber being limited to translational movement within the chamber. The piston preferably having a threaded rod extending therefrom that engages with a threaded aperture in an actuator such that advancement of the piston toward the dispensing end occurs when the actuator is rotated. Rotation of the actuator causes the product to be dispensed from the dispensing end. An applicator is preferably attached to the dispensing end of the housing in fluid communication with the chamber wherein the product is dispensed through the applicator. The applicator can comprise a ferrule and an application portion wherein the ferrule is attached to the dispensing end of the housing and the application portion has at least one orifice located therein. Several versions of applicators can be utilized including, for example, a fiber brush or an application surface having flocking thereon. Flocking is a mat of thin, short, plastic fibers substantially perpendicular to the application surface. The bristles of a fiber brush are preferably tapered and made of a plastic material. Alternatively, the user may use a more traditional applicator or implement known in the art.

As stated above, the user applies the composition directly to the lips wherein the user allows the composition to dry before subjecting the composition to insult. Once the composition is dried, a complimentary product such as the topcoat product disclosed above may be applied over the dried product to provide the user with an asthetically pleasing affect. Topcoat compositions may utilize the same dispensing device as discribed for use of the compositions of the present invention.

The compositions of the present invention may be removed by applying petrolatum or a dimethicone-based cosmetic remover to the skin or lips and rubbing the area gently with a tissue to remove the cosmetic.

EXAMPLES

The following examples illustrate the examples of the claimed cosmetic compositions of the present invention but are not intended to be limiting thereof:

EXAMPLE 1

| Ingredients | Weight (%) |
|---|---|
| Group A: | |
| Silicone Gum[1] | 10.91 |
| Isododecane[2] | 50.00 |
| Group B: | |
| Organosiloxane resin[3] | 19.09 |
| Red #6 Calcium Lake | 3.00 |
| Red #7 Barium Lake | 3.00 |
| Titanium Dioxide | 3.00 |
| Blue | 0.50 |
| Brown | 0.50 |
| Bentone Gel[4] | 10.00 |

[1] 1,000,000 cSt Dimethicone Gum available as SE 30 from General Electric.
[2] Permethyl 99A available from Permethyl Corporation.
[3] MQ Resin (0.7:1 ratio M:Q) available as 1170-002 from General Electric.
[4] VS-5 PC available from Rheox.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Transfer the resulting fluid to individual packages.

EXAMPLE 2

| Ingredient | Weight (%) |
|---|---|
| Group A: | |
| Organosiloxane resin[1] | 19.20 |
| Isododecane[2] | 14.90 |
| Group B: | |
| Red #6 Calcium Lake | 1.49 |
| Red #7 Barium Lake | 2.10 |
| Titanium Dioxide | 2.33 |
| Blue | 1.03 |
| Brown | 3.00 |
| Propylparaben | 0.15 |
| Group C: | |
| Silicone Gum[3] | 10.80 |
| Isododecane[2] | 33.00 |

-continued

| Ingredient | Weight (%) |
|---|---|
| Group D: | |
| Isododecane[2] | 10.00 |
| Trihydroxystearin | 2.00 |

[1] MQ Resin (0.7:1 ratio M:Q) available as MQ 804 from Wacker Silicones Corp.
[2] Permethyl 99A available from Permethyl Corp.
[3] Dimethicone Gum (2,500,000 cSt) available as SE 30 from General Electric.

Combine Group A ingredients together and mix with a propeller mixer until uniform. Add Group B ingredients to Group A mixture and homogenize until the pigments are completely dispersed. Premix Group C ingredients in a separate container using a propeller mixer until uniform, then combine with the mixture of Groups A and B ingredients. Premix Group D ingredients wit heating to about 57–60° C. for about 3 minutes. Remove from the heat and homogenize for approximately five minutes or until a gel develops. Finally, add the Group D mixture to the rest of the batch and heat the entire mixture to 57–60° C. for about 7 to 10 minutes while mixing with a propeller mixer. Remove the batch from the heat and allow it to cool to room temperature while mixing with a propeller mixer. Transfer the resulting fluid to individual packages.

EXAMPLE 3

| Ingredients | Weight (%) |
|---|---|
| Group A: | |
| Dimethicone Fluid[1] | 8.40 |
| Octamethylcyclotetrasiloxane[2] | 30.80 |
| Group B: | |
| Organosiloxane resin[3] | 14.70 |
| Red #6 Calcium Lake | 2.30 |
| Red #7 Barium Lake | 2.30 |
| Titanium Dioxide | 2.30 |
| Blue | 0.38 |
| Brown | 0.38 |
| Emulsifier[4] | 7.70 |
| Propylene Glycol | 0.74 |
| Group C: | |
| Water | 29.25 |
| D&C Red 33 | 0.30 |
| D&C Green 5 | 0.10 |
| D&C Yellow 5 | 0.10 |
| Methylparben | 0.25 |

[1] 100,000 cSt Dimethicone Fluid available from General Electric.
[2] Octamethylcyclotetrasiloxane available from General Electric.
[3] MQ Resin (0.7:1 ratio M:Q) available as 1170-002 from General Electric.
[4] Dow Corning 3225C available from Dow Corning.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Premix Group C ingredients with a propeller mixer until uniform. Homogenize the mixture of Groups A and B ingredients while adding the Group C mixture slowly to create a stable emulsion. When addition of the Group C mixture is complete, homogenize the entire formula for ten more minutes. Transfer the resulting fluid to individual packages.

EXAMPLE 4

| Ingredients | Weight (%) |
|---|---|
| Group A: | |
| Silicone Gum[1] | 16.20 |
| Octamethylcyclotetrasiloxane[2] | 70.00 |
| Group B: | |
| Organosiloxane resin[3] | 1.80 |
| Red #6 Calcium Lake | 1.80 |
| Red #7 Barium Lake | 1.80 |
| Titanium Dioxide | 1.80 |
| Blue | 0.30 |
| Brown | 0.30 |
| Bentone Gel[4] | 6.00 |

[1] 2,500,000 cSt Dimethicone Gum available as SE 63 from General Electric.
[2] Octamethylcyclotetrasiloxane available from General Electric.
[3] MQ Resin (0.7:1 ratio M:Q) available as 1170-002 from General Electric.
[4] VS-5 PC available from Rheox.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Transfer the resulting fluid to individual packages.

EXAMPLE 5

| Ingredients | Weight (%) |
|---|---|
| Group A: | |
| Silicone Gum[1] | 10.80 |
| Isododecane[2] | 43.58 |
| Group B: | |
| Organosiloxane resin[3] | 19.20 |
| Red #6 Calcium Lake | 1.50 |
| Red #7 Barium Lake | 1.23 |
| Titanium Dioxide | 2.00 |
| Russet | 1.43 |
| Brown | 0.31 |
| Mica | 2.65 |
| Propylparaben | 0.10 |
| Bentone Gel[4] | 9.90 |
| Group C: | |
| Emulsifier[5] | 2.15 |
| Glycerin | 5.00 |
| Methylparaben | 0.15 |

[1] 2,500,000 cSt Dimethicone Gum available as SE 63 from General Electric.
[2] Permethyl 99A available from Permethyl Corp.
[3] MT Resin available from Toshiba Silicones.
[4] VS-5 PC available from Rheox.
[5] Dow Corning 3225C available from Dow Corning.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Premix Group C ingredients with a propeller mixer until uniform. Homogenize the mixture of Groups A and B ingredients while adding the Group C mixture slowly to create a stable emulsion. When addition of the Group C mixture is complete, homogenize the entire formula for ten more minutes. Transfer the resulting fluid to individual packages.

EXAMPLE 6

| Ingredients | Weight (%) |
|---|---|
| Group A: | |
| Silicone Gum[1] | 10.91 |
| Isododecane[2] | 58.00 |
| Group B: | |
| Organosiloxane resin[3] | 19.09 |
| Red #6 Calcium Lake | 3.00 |
| Red #7 Barium Lake | 3.00 |
| Titanium Dioxide | 3.00 |
| Blue | 0.50 |
| Brown | 0.50 |
| Group C: | |
| Unlin 425[4] | 2.00 |

[1]·2,500,000 cSt Dimethicone Gum available as SE 63 from General Electric.
[2]·Permethyl 99A available from Permethyl Corp.
[3]·MQ Resin (0.7:1 ratio M:Q) available as 1170-002 from General Electric.
[4]·Unlin 425 available from Petrolite Corporation.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Premix Group C ingredients with a propeller mixer until uniform. Heat the mixture of Groups A and B ingredients together with the Group C wax to 70° C. while mixing with a propeller mixer. When the wax is melted and the mixture is homogeneous, cool the entire formula to room temperature without mixing. Transfer the resulting fluid to individual packages.

EXAMPLE 7

| Ingredients | Weight (%) |
|---|---|
| Group A: | |
| Dimethicone Fluid[1] | 19.09 |
| Isododecane[2] | 20.00 |
| Group B: | |
| Organosiloxane resin[3] | 33.42 |
| Red #6 Calcium Lake | 5.25 |
| Red #7 Barium Lake | 5.25 |
| Titanium Dioxide | 5.25 |
| Blue | 0.87 |
| Brown | 0.87 |
| Bentone Gel[4] | 10.00 |

[1]·1,000 cSt Dimethicone Fluid available from General Electric.
[2]·Permethyl 99A available from Permethyl Corp.
[3]·MQ Resin (0.7:1 ratio M:Q) available as 1170-002 from General Electric.
[4]·VS-5 PC available from Rheox.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Transfer the resulting fluid to individual packages.

EXAMPLE 8

| Ingredients | Weight (%) |
|---|---|
| Group A: | |
| Silicone Gum[1] | 12.88 |
| Octamethylcyclotetrasiloxane[2] | 20.00 |
| Group B: | |
| Organosiloxane resin[3] | 39.63 |
| Red #6 Calcium Lake | 5.25 |
| Red #7 Barium Lake | 5.25 |
| Titanium Dioxide | 5.25 |
| Blue | 0.87 |
| Brown | 0.87 |
| Bentone Gel[4] | 10.00 |

[1]·2,500,000 cSt Dimethicone Gum available as SE 63 from General Electric.
[2]·Octamethylcyclotetrasiloxane available from General Electric.
[3]·MQ Resin (0.7:1 ratio M:Q) available as 1170-002 from General Electric.
[4]·VS-5 PC available from Rheox.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Transfer the resulting fluid to individual packages.

EXAMPLE 9

| Ingredients | Weight (%) |
|---|---|
| Group A: | |
| Silicone Gum[1] | 11.88 |
| Isododecane[2] | 54.45 |
| Group B: | |
| Organosiloxane resin[3] | 20.78 |
| Red #6 Calcium Lake | 0.50 |
| Red #7 Barium Lake | 0.50 |
| Titanium Dioxide | 0.50 |
| Mica | 0.50 |
| Bentone Gel[4] | 10.89 |

[1]·2,500,000 cSt Dimethicone Gum available as SE 63 from General Electric.
[2]·Permethyl 99A available from Permethyl Corp.
[3]·MQ Resin (0.7:1 ratio M:Q) available as 1170-002 from General Electric.
[4]·VS-5 PC available from Rheox.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Transfer the resulting fluid to individual packages.

EXAMPLE 10

| Ingredients | Weight (%) |
|---|---|
| Group A: | |
| Silicone Gum[1] | 10.47 |

-continued

| Ingredients | Weight (%) |
|---|---|
| Isododecane[2] | 47.61 |
| Group B: | |
| Organosiloxane resin[3] | 18.32 |
| Red #6 Calcium Lake | 4.00 |
| Red #7 Barium Lake | 4.00 |
| Titanium Dioxide | 1.00 |
| Blue | 1.00 |
| Brown | |
| Bentone Gel[4] | 9.60 |

[1]·2,500,000 cSt Dimethicone Gum available as SE 63 from General Electric.
[2]·Permethyl 99A available from Permethyl Corp.
[3]·MQ Resin (0.7:1 ratio M:Q) available as 1170-002 from General Electric.
[4]·VS-5 PC available from Rheox.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Transfer the resulting fluid to individual packages.

EXAMPLE 11

| Ingredient | Weight (%) |
|---|---|
| Group A: | |
| Organosiloxane resin[1] | 19.20 |
| Isododecane[2] | 14.90 |
| Group B: | |
| Red #6 Calcium Lake | 1.49 |
| Red #7 Barium Lake | 2.10 |
| Titanium Dioxide | 2.33 |
| Blue | 1.03 |
| Brown | 3.00 |
| Propylparaben | 0.15 |
| Group C: | |
| Silicone Gum[3] | 10.80 |
| Isododecane[2] | 33.00 |
| Group D: | |
| Isododecane[2] | 10.00 |
| Trihydroxystearin | 2.00 |

[1]·MQ Resin (0.7:1 ratio M:Q) available as MQ 803 from Wacker Silicones Corp.
[2]·Permethyl 99A available from Permethyl Corp.
[3]·2,500,000 cSt Dimethicone Gum available as SE 63 from General Electric.

Combine Group A ingredients together and mix with a propeller mixer until uniform. Add Group B ingredients to Group A mixture and homogenize until the pigments are completely dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately five minutes or until a gel develops. Finally, add the Group D mixture to the rest of the batch and heat the entire mixture to 57–60° C. for about 7 to 10 minutes while mixing with a propeller mixer. Remove the batch from the heat and allow it to cool to room temperature while mixing with a propeller mixer. Transfer the resulting fluid to individual packages.

EXAMPLE 12

| Ingredient | Weight (%) |
|---|---|
| Group A: | |
| Organosiloxane Resin[1] | 11.90 |
| Isododecane[2] | 14.90 |
| Group B: | |
| Red #6 Calcium Lake | 3.00 |
| Red #7 Barium Lake | 4.20 |
| Titanium Dioxide | 4.70 |
| Blue | 2.05 |
| Brown | 6.05 |
| Propylparaben | 0.10 |
| Group C: | |
| 1,000 cSt Silicone Fluid[3] | 8.10 |
| Isododecane[2] | 33.00 |
| Group D: | |
| Isododecane[2] | 10.00 |
| Trihydroxystearin | 2.00 |

[1]·MQ Resin (0.7:1 ratio M:Q) available as 1170-002 from General Electric.
[2]·Permethyl 99A available from Permethyl Corp.
[3]·Dimethicone Fluid (1,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 13

| Ingredient | Weight (%) |
|---|---|
| Group A: | |
| Organosiloxane Resin[1] | 22.14 |
| Isododecane[2] | 14.90 |
| Group B: | |
| Red #6 Calcium Lake | 0.60 |
| Red #7 Barium Lake | 0.84 |
| Titanium Dioxide | 0.94 |
| Blue | 0.41 |
| Brown | 1.21 |
| Propylparaben | 0.10 |
| Group C: | |
| 1,000 cSt Silicone Fluid[3] | 13.86 |
| Isododecane[2] | 33.00 |

-continued

| Ingredient | Weight (%) |
|---|---|
| Group D: | |
| Isododecane[2] | 10.00 |
| Trihydroxystearin | 2.00 |

[1] MQ Resin (0.7:1 ratio M:Q) available as 1170-002 from General Electric.
[2] Permethyl 99A available from Permethyl Corp.
[3] Dimethicone Fluid (1,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, them combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 14

| Ingredient | Weight (%) |
|---|---|
| Group A: | |
| Organosiloxane Resin[1] | 26.00 |
| Isododecane[2] | 14.90 |
| Group B: | |
| Red #6 Calcium Lake | 0.60 |
| Red #7 Barium Lake | 0.84 |
| Titanium Dioxide | 0.94 |
| Blue | 0.41 |
| Brown | 1.21 |
| Propylparaben | 0.10 |
| Group C: | |
| 1,000 cSt Silicone Fluid[3] | 10.00 |
| Isododecane[2] | 33.00 |
| Group D: | |
| Isododecane[2] | 10.00 |
| Trihydroxystearin | 2.00 |

[1] MQ Resin (0.7:1 ratio M:Q) available as 1170-002 from General Electric.
[2] Permethyl 99A available from Permethyl Corp.
[3] Dimethicone Fluid (1,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 15

| Ingredient | Weight (%) |
|---|---|
| Group A: | |
| Organosiloxane Resin[1] | 8.90 |
| Isododecane[2] | 14.90 |
| Group B: | |
| Red #6 Calcium Lake | 3.00 |
| Red #7 Barium Lake | 4.20 |
| Titanium Dioxide | 4.70 |
| Blue | 2.05 |
| Brown | 6.05 |
| Propylparaben | 0.10 |
| Group C: | |
| 100,000 cSt Silicone Fluid[3] | 11.10 |
| Isododecane[2] | 33.00 |
| Group D: | |
| Isododecane[2] | 10.00 |
| Trihydroxystearin | 2.00 |

[1] MQ Resin (0.7:1 ratio M:Q) available as 1170-002 from General Electric.
[2] Permethyl 99A available from Permethyl Corp.
[3] Dimethicone Fluid (100,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 16

| Ingredient | Weight (%) |
|---|---|
| Group A: | |
| Organosiloxane Resin[1] | 11.70 |
| Isododecane[2] | 14.90 |
| Group B: | |
| Red #6 Calcium Lake | 3.00 |
| Red #7 Barium Lake | 4.20 |
| Titanium Dioxide | 4.70 |
| Blue | 2.05 |
| Brown | 6.05 |
| Propylparaben | 0.10 |
| Group C: | |
| 100,000 cSt Silicone Fluid[3] | 8.30 |
| Isododecane[2] | 33.00 |

-continued

| Ingredient | Weight (%) |
|---|---|
| Group D: | |
| Isododecane[2] | 10.00 |
| Trihydroxystearin | 2.00 |

[1]MQ Resin (0.7:1 ratio M:Q) available as 1170-002 from General Electric.
[2]Permethyl 99A available from Permethyl Corp.
[3]Dimethicone Fluid (100,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 17

| Ingredient | Weight (%) |
|---|---|
| Group A: | |
| Organosiloxane Resin[1] | 22.14 |
| Isododecane[2] | 14.90 |
| Group B: | |
| Red #6 Calcium Lake | 0.60 |
| Red #7 Barium Lake | 0.84 |
| Titanium Dioxide | 0.94 |
| Blue | 0.41 |
| Brown | 1.21 |
| Propylparaben | 0.10 |
| Group C: | |
| 100,000 cSt Silicone Fluid[3] | 13.86 |
| Isododecane[2] | 33.00 |
| Group D: | |
| Isododecane[2] | 10.00 |
| Trihydroxystearin | 2.00 |

[1]MQ Resin (0.7:1 ratio M:Q) available as 1170-002 from General Electric.
[2]Permethyl 99A available from Permethyl Corp.
[3]Dimethicone Fluid (100,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 18

| Ingredient | Weight (%) |
|---|---|
| Group A: | |
| Organosiloxane Resin[1] | 26.00 |
| Isododecane[2] | 14.90 |
| Group B: | |
| Red #6 Calcium Lake | 0.60 |
| Red #7 Barium Lake | 0.84 |
| Titanium Dioxide | 0.94 |
| Blue | 0.41 |
| Brown | 1.21 |
| Propylparaben | 0.10 |
| Group C: | |
| 100,000 cSt Silicone Fluid[3] | 10.00 |
| Isododecane[2] | 33.00 |
| Group D: | |
| Isododecane[2] | 10.00 |
| Trihydroxystearin | 2.00 |

[1]MQ Resin (0.7:1 ratio M:Q) available as 1170-002 from General Electric.
[2]Permethyl 99A available from Permethyl Corp.
[3]Dimethicone Fluid (100,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 19

| Ingredient | Weight (%) |
|---|---|
| Group A: | |
| Organosiloxane Resin[1] | 3.34 |
| Isododecane[2] | 14.90 |
| Group B: | |
| Red #6 Calcium Lake | 3.00 |
| Red #7 Barium Lake | 4.20 |
| Titanium Dioxide | 4.70 |
| Blue | 2.05 |
| Brown | 6.05 |
| Propylparaben | 0.10 |
| Group C: | |
| 2,500,000 cSt Silicone Gum[3] | 16.66 |
| Isododecane[2] | 33.00 |

-continued

| Ingredient | Weight (%) |
|---|---|
| Group D: | |
| Isododecane[2] | 10.00 |
| Trihydroxystearin | 2.00 |

[1] MQ Resin (0.7:1 ratio M:Q) available as 1170-002 from General Electric.
[2] Permethyl 99A available from Permethyl Corp.
[3] Dimethicone Gum (2,500,000 cSt) available as SE63 from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 20

| Ingredient | Weight (%) |
|---|---|
| Group A: | |
| Organosiloxane Resin[1] | 11.70 |
| Isododecane[2] | 14.90 |
| Group B: | |
| Red #6 Calcium Lake | 3.00 |
| Red #7 Barium Lake | 4.20 |
| Titanium Dioxide | 4.70 |
| Blue | 2.05 |
| Brown | 6.05 |
| Propylparaben | 0.10 |
| Group C: | |
| 2,500,000 cSt Silicone Gum[3] | 8.30 |
| Isododecane[2] | 33.00 |
| Group D: | |
| Isododecane[2] | 10.00 |
| Trihydroxystearin | 2.00 |

[1] MQ Resin (0.7:1 ratio M:Q) available as 1170-002 from General Electric.
[2] Permethyl 99A available from Permethyl Corp.
[3] Dimethicone Gum (2,500,000 cSt) available as SE63 from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 21

| Ingredient | Weight (%) |
|---|---|
| Group A: | |
| Organosiloxane Resin[1] | 20.68 |
| Isododecane[2] | 14.90 |
| Group B: | |
| Red #6 Calcium Lake | 0.60 |
| Red #7 Barium Lake | 0.84 |
| Titanium Dioxide | 0.94 |
| Blue | 0.41 |
| Brown | 1.21 |
| Propylparaben | 0.10 |
| Group C: | |
| 2,500,000 cSt Silicone Gum[3] | 15.32 |
| Isododecane[2] | 33.00 |
| Group D: | |
| Isododecane[2] | 10.00 |
| Trihydroxystearin | 2.00 |

[1] MQ Resin (0.7:1 ratio M:Q) available as 1170-002 from General Electric.
[2] Permethyl 99A available from Permethyl Corp.
[3] Dimethicone Gum (2,500,000 cSt) available as SE63 from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 22

| Ingredient | Weight (%) |
|---|---|
| Group A: | |
| Organosiloxane Resin[1] | 27.80 |
| Isododecane[2] | 14.90 |
| Group B: | |
| Red #6 Calcium Lake | 0.60 |
| Red #7 Barium Lake | 0.84 |
| Titanium Dioxide | 0.94 |
| Blue | 0.41 |
| Brown | 1.21 |
| Propylparaben | 0.10 |
| Group C: | |
| 2,500,000 cSt Silicone Gum[3] | 8.20 |
| Isododecane[2] | 33.00 |

-continued

| Ingredient | Weight (%) |
|---|---|
| Group D: | |
| Isododecane[2] | 10.00 |
| Trihydroxystearin | 2.00 |

[1] MQ Resin (0.7:1 ratio M:Q) available as 1170-002 from General Electric.
[2] Permethyl 99A available from Permethyl Corp.
[3] Dimethicone Gum (2,500,000 cSt) available as SE63 from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 23

| Ingredient | Weight (%) |
|---|---|
| Group A: | |
| Organosiloxane Resin[1] | 19.20 |
| Isododecane[2] | 14.90 |
| Group B: | |
| Red #6 Calcium Lake | 1.49 |
| Red #7 Barium Lake | 2.10 |
| Titanium Dioxide | 2.33 |
| Blue | 1.03 |
| Brown | 3.00 |
| Propylparaben | 0.15 |
| Group C: | |
| Phenylmethyl Silicone Gum[3] | 10.80 |
| Isododecane[2] | 33.00 |
| Group D: | |
| Isododecane[2] | 10.00 |
| Trihydroxystearin | 2.00 |

[1] MQ Resin available as 1170-002 from General Electric.
[2] Permethyl 99A available from Permethyl Corp.
[3] Phenylmethyl Silicone Gum available as 88778 from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 24

| Ingredient | Weight (%) |
|---|---|
| Group A: | |
| Organosiloxane Resin[1] | 19.20 |
| Isododecane[2] | 14.90 |
| Group B: | |
| Red #6 Calcium Lake | 1.49 |
| Red #7 Barium Lake | 2.10 |
| Titanium Dioxide | 2.33 |
| Blue | 1.03 |
| Brown | 3.00 |
| Propylparaben | 0.15 |
| Group C: | |
| 2,500,000 cSt Silicone Gum[3] | 5.00 |
| 10,000 cSt Silicone Fluid[4] | 5.80 |
| Isododecane[2] | 33.00 |
| Group D: | |
| Isododecane[2] | 10.00 |
| Trihydroxystearin | 2.00 |

[1] MQ Resin (0.7:1 ratio M:Q) available as 1170-002 from General Electric.
[2] Permethyl 99A available from Permethyl Corp.
[3] Dimethicone Gum (2,500,000 cSt) available as SE63 from General Electric.
[4] Dimethicone Fluid (10,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

EXAMPLE 25

| Ingredients | Weight (%) |
|---|---|
| Group A: | |
| Silicone Gum[1] | 12.60 |
| Isododecane[2] | 12.60 |
| Group B: | |
| Isododecane[2] | 43.38 |
| Bentonite Clay[4] | 1.00 |
| Propylene Carbonate | 0.32 |
| Red #6 Calcium Lake | 1.00 |
| Red #7 Barium Lake | 3.00 |
| Titanium Dioxide | 1.50 |
| Mica | 2.20 |
| Organosiloxane resin[3] | 22.40 |

[1,2] 2,500,000 cst Dimethicone Gum available as SE 63 from General Electric.
[2] Permethyl 99A available from Permethyl Corp.
[3] MQ Resin (0.7:1 ratio M:Q) available as 1170-002 from General Electric.
[4] Bentone 38 available from Rheox.

Combine Group A ingredients together in a beaker and mix with a propeller mixer until uniform. Combine all Group B ingredients except the propylene carbonate and hand-mix to roughly incorporate the dry powders. Homogenize the entire formulation using a Ross ME 100 LC homogenizer at about 7500 rpm until all pigments are fully dispersed. Next, while continuing the homogenization process, slowly add the propylene carbonate until mixture thickens. Combine Group A mixture with Group B mixture in a beaker and mix with a propeller mixer until uniform. Transfer the resulting fluid to individual packages.

We claim:

1. A cosmetic composition for application to the lips, which composition comprises:
   A) a mixture of:
      (1) an organosiloxane resin; and
      (2) a fluid diorganopolysiloxane polymer having a viscosity of from about 1,000,000 cSt to 10,000,000 cSt at 25° C.;
      wherein the ratio of (1) to (2) is from about 1:9 to about 20:1; and
   B) a volatile carrier.

2. The cosmetic composition according to claim 1 which upon application the forms a transfer resistant film as measured by dry blot and rub test and oil blot and rub test, each test resulting in an average normalized reflectance of about 50% or greater.

3. A cosmetic composition for application to the lips which upon application forms a transfer resistant, flexible film wherein the film's flexibility is measured by a flexibility test resulting in an average percent weight loss of about 30% or less, and the film's transfer resistance is measured by a dry blot and rub test and an oil blot and rub test, each test resulting in an average normalized reflectance of about 50% or greater.

4. The cosmetic composition according to claim 3 comprising:
   a. an organosiloxane resin;
   b. a fluid diorganopolysiloxane polymer;
   c. a pigment; and
   d. a volatile carrier which solubilizes said organosiloxane resin;
wherein the fluid diorganopolysiloxane polymer to pigment ratio is from about 1:1 to about 30:1, the ratio of organosiloxane resin to fluid diorganopolysiloxane polymer is from about 1:10 to about 3.5:1, and said composition comprises no more than about 2% by weight of waxes.

5. The cosmetic composition according to claim 4 wherein the organosiloxane resin comprises $R_3SiO_{1/2}$ "M" units, $R_2SiO$ "D" units, $RSiO_{3/2}$ "T" units, $SiO_2$ "Q" units and mixtures thereof in a ratio selected to satisfy the relationship $R_nSiO_{(4-n)/2}$, wherein n is from about 1.0 to about 1.50 and R is a methyl group, wherein the resin is solid at about 25° C., has a molecular weight range from about 1,000 to about 10,000 grams/mole and is soluble in organic solvents.

6. The cosmetic composition according to claim 5 wherein organosiloxane resin comprises $R_3SiO_{1/2}$ "M" units and $SiO_2$ "Q" units wherein the ratio of $R_3SiO_{1/2}$ to $SiO_2$ is about 0.7 wherein n is about 1.2.

7. The cosmetic composition according to claim 6 wherein the fluid diorganopolysiloxane polymers comprise repeating units of the formula ($R_2SiO$), where R is a hydrocarbon side group having from 1 to 6 carbon atoms.

8. The cosmetic composition according to claim 7 wherein said hydrocarbon side group is selected from the group consisting of methyl, ethyl, propyl, isopropyl, butyl, isobutyl, t-butyl, amyl, hexyl, vinyl, allyl, cyclohexyl, amino alkyl, phenyl, fluoroalkyl and mixtures thereof.

9. The cosmetic composition according to claim 8 wherein fluid diorganopolysiloxane polymer is terminated by triorganosilyl groups of the formula ($R'_3Si$) where R' is a monovalent hydrocarbon radical selected from the group consisting of 1 to 6 carbon atoms, hydroxyl groups, an alkoxyl groups and mixtures thereof.

10. The cosmetic composition according to claim 9 wherein fluid diorganopolysiloxane polymer is polydimethyl siloxane.

11. The cosmetic composition according to claim 4 wherein the volatile carrier is selected from the group consisting of hydrocarbon oils, silicone oils and mixtures thereof.

12. The cosmetic composition according to claim 10 wherein the volatile carrier is isododecane.

13. A cosmetic composition for application to the lips, which composition comprises:
   a. an organosiloxane resin comprising $R_3SiO_{1/2}$ "M" units, $R_2SiO$ "D" units, $RSiO_{3/2}$ "T" units, $SiO_2$ "Q" units and mixtures thereof in a ratio selected to satisfy the relationship $R_nSiO_{(4-n)/2}$, wherein n is from about 1.0 to about 1.50 and R is a methyl group;
   b. a fluid diorganopolysiloxane polymer,
   c. a pigment; and
   d. a volatile carrier capable of solubilizing said organosiloxane resin;
wherein the fluid diorganopolysiloxane polymer has a viscosity greater than 600,000 cSt at 25° C., the fluid diorganopolysiloxane polymer to pigment ratio is from about 1:1 to about 30:1, and the ratio of organosiloxane resin to fluid diorganopolysiloxane polymer is from about 1:10 to about 3.5:1.

14. The cosmetic composition according to claim 13 wherein the organosiloxane resin comprises $R_3SiO_{1/2}$ "M" units, $R_2SiO$ "D" units, $RSiO_{3/2}$ "T" units, $SiO_2$ "Q" units and mixtures thereof in a ratio selected to satisfy the relationship $R_nSiO_{(4-n)/2}$, wherein n is from about 1.0 to about 1.50 and R is methyl group.

15. The cosmetic composition according to claim 13 wherein organosiloxane resin comprises $R_3SiO_{1/2}$ "M" units and $SiO_2$ "Q" units wherein the ratio of $R_3SiO_{1/2}$ to $SiO_2$ is about 0.7 wherein n is about 1.2.

16. The cosmetic composition according to claim 13 wherein the fluid diorganopolysiloxane polymers comprise repeating units of the formula ($R_2SiO$), where R is a hydrocarbon side group having from 1 to 6 carbon atoms.

17. The cosmetic composition according to claim 16 wherein said hydrocarbon side group is selected from the group consisting of methyl, ethyl, propyl, isopropyl, butyl, isobutyl, t-butyl, amyl, hexyl, vinyl, allyl, cyclohexyl, amino alkyl, phenyl, fluoroalkyl and mixtures thereof.

18. The cosmetic composition according to claim 17 wherein fluid diorganopolysiloxane polymer is terminated by triorganosilyl groups of the formula ($R'_3Si$) where R' is a monovalent hydrocarbon radical selected from the group consisting of 1 to 6 carbon atoms, hydroxyl groups, an alkoxyl groups and mixtures thereof.

19. The cosmetic composition according to claim 18 wherein fluid diorganopolysiloxane polymer is polydimethyl siloxane.

20. The cosmetic composition according to claim 13 wherein the volatile carrier is selected from the group consisting of hydrocarbon oils, silicone oils and mixtures thereof.

21. The cosmetic composition according to claim 20 wherein the volatile carrier is isododecane.

22. A method of applying the composition of claim 3 comprising the steps of:

a. applying the composition from a suitable cosmetic applicator directly onto the lips; and b. allowing said composition to form a dry film.

23. The method according to claim 22 additionally comprising the step of applying a complimentary product on said dried film where upon applying said complimentary product said composition is not disrupted.

* * * * *

UNITED STATES PATENT AND TRADEMARK OFFICE
CERTIFICATE OF CORRECTION

PATENT NO. : 6,074,654
DATED : June 13, 2000
INVENTOR(S) : Drechsler et al.

It is certified that error appears in the above-identified patent and that said Letters Patent is hereby corrected as shown below:

Title page,
Line 21, of U.S. PATENTS DOCEMENTS, should read
-- "5,505,937    4/96    Castrogiovanni et al.    424/64 --.
Under line 21 of U.S. PATENT DOCUMENTS, insert new line to read
-- 5,512,272    4/96    Krzysik    424/59 --.

Column 1,
Line 62, "at" should read -- as --.

Column 3,
Line 6, "But" should read -- By --.
Line 16, "sampler" should read -- sample --.
Line 41, "Attache" should read -- Attach --.
Line 41, "collage" should read -- collagen --.

Column 4,
Line 39, "oil" should read -- oily --.

Column 8,
Line 44, "diorganosiloxane" should read -- diorganopolysiloxane --.

Column 9,
Line 46, "polymer" should read -- polymers --.

Column 10,
Line 52, "Once" should read -- One --.
Line 55, "compositions" should read -- composition --.
Line 64, "compositions" should read -- composition --.

Column 11,
Line 58, "88.30" should read -- 90.30 --.

Column 12,
Line 63, "in" should read -- is --.

Column 14,
Line 16, "group" should read -- Group --.

UNITED STATES PATENT AND TRADEMARK OFFICE
CERTIFICATE OF CORRECTION

PATENT NO. : 6,074,654
DATED : June 13, 2000
INVENTOR(S) : Drechsler et al.

It is certified that error appears in the above-identified patent and that said Letters Patent is hereby corrected as shown below:

Column 15,
Line 22, "METHODS" should read -- METHOD --.
Line 33, "To" should read -- to --.

Column 17,
Line 51, "Methylparben" should read -- Methylparaben --.

Signed and Sealed this

Ninth Day of October, 2001

Attest:

*Nicholas P. Godici*

NICHOLAS P. GODICI
*Attesting Officer*  *Acting Director of the United States Patent and Trademark Office*

UNITED STATES PATENT AND TRADEMARK OFFICE
CERTIFICATE OF CORRECTION

PATENT NO.   : 6,074,654
DATED        : June 13, 2000
INVENTOR(S)  : Drechsler et al.

It is certified that error appears in the above-identified patent and that said Letters Patent is hereby corrected as shown below:

Column 21,
Line 10, the line "Titanium Dioxide   1.00" should read -- Titanium Dioxide   4.00 --.
Line 12, the line "Brown" should read -- Brown   1.00 --.

Column 23,
Line 17, "them" should read -- then --.

Signed and Sealed this

Sixth Day of August, 2002

Attest:

JAMES E. ROGAN
Attesting Officer  Director of the United States Patent and Trademark Office